United States Patent [19]

Orr et al.

[11] 4,120,975
[45] Oct. 17, 1978

[54] METHOD OF PSYCHIATRIC CONDITIONS

[75] Inventors: Thomas Samuel Campbell Orr, Melton Mowbray; Patrick John Kingsley, Belton, Nr. Loughborough, both of England

[73] Assignee: Fisons Limited, London, England

[21] Appl. No.: 831,537

[22] Filed: Sep. 8, 1977

Related U.S. Application Data

[63] Continuation-in-part of Ser. No. 717,875, Aug. 26, 1976, Pat. No. 4,067,992.

[30] Foreign Application Priority Data

Sep. 15, 1976 [GB] United Kingdom ............... 38101/76
Jun. 25, 1977 [GB] United Kingdom ............... 26732/77

[51] Int. Cl.² .......................................... A61K 31/35
[52] U.S. Cl. .................................................. 424/283
[58] Field of Search ........................................ 421/283

[56] References Cited

U.S. PATENT DOCUMENTS 3,484,445  12/1969  Lee et al. ............................. 424/283
3,952,013  4/1976  Hazard et al. ....................... 424/283

Primary Examiner—Stanley J. Friedman
Attorney, Agent, or Firm—Merriam, Marshall & Bicknell

[57] ABSTRACT

There is described a method of treatment of certain psychiatric conditions which method comprises administration of a compound of the formula I,

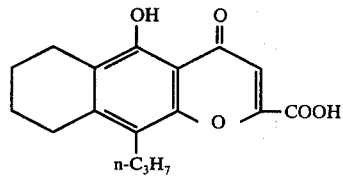

or a therapeutically acceptable salt, ester or amide thereof, (as active ingredient), to a patient having such a condition.

10 Claims, No Drawings

METHOD OF PSYCHIATRIC CONDITIONS

This application is a continuation-in-part of our co-pending application Ser. No. 717,875, filed Aug. 26, 1976, now U.S. Pat. No. 4,067,992, issued Jan. 10, 1978.

This invention relates to a new therapeutic method.

According to the invention there is provided a method of treatment of psychiatric conditions in mammals which method comprises administration of a compound of the formula I,

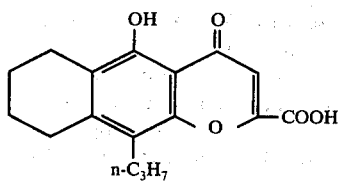

or a therapeutically acceptable salt, alkyl C 1 to 10 ester, mono-alkyl C 1 to 10 amide, di-alkyl C 1 to 10 amide or an unsubstituted amide thereof, as active ingredient, to a patient suffering or liable to suffer, from such a condition.

Suitable pharmaceutically acceptable salts include, for example, ammonium salts, alkali metal salts (e.g. sodium, potassium and lithium), alkaline earth metal salts (e.g. magnesium and calcium), and salts with organic amines (e.g. monodi- or tri- alkyl C 1 to 6 amines, piperidine, and trialkanol C 1 to 6 amine salts). Esters which may be mentioned include simple alkyl esters (e.g. methyl, ethyl, propyl, isopropyl, butyl and tertiary butyl esters) and amides which may be mentioned include simple amides (for example amides with ammonia and lower alkylamines such as methylamine, ethylamine etc).

The active ingredient may be administered to mammals, particularly humans.

The active ingredient is preferably administered as a conventional oral composition. The active ingredient may also be administered by other means, e.g. rectally (as a suppository or enema), topically, by injection or by means of a depot preparation.

In order to produce suitable compositions the active ingredient is worked up with inorganic or organic pharmaceutically acceptable adjuvants or excipients. Examples of such adjuvants are:

For tablets and dragees: Binders, for example, cellulosic materials, e.g. microcrystalline cellulose and methyl cellulose; disintegrating agents, for example starches, e.g. maize starch; stabilisers, e.g. against hydrolysis of the active ingredients; flavouring agents, for example sugars such as lactose; fillers; stearates and inorganic diluents, e.g. talc.

For syrups, suspensions or dispersions: A liquid vehicle in which the active ingredients may be dissolved or suspeneded e.g. water; and suspending agents, e.g. cellulose derivatives, gums etc.

For hard or soft capsules: diluents, e.g. lactose; glidants, e.g. stearates; inorganic materials, e.g. silica or talc; stabilisers and dispersing agents.

The composition may also contain further adjuvants, for example a composition for use in tablets may contain lubricants and glidants to assist in tabletting, e.g. magnesium stearate, or wetting agents to assist in granulation, e.g. dioctyl sodium sulphosuccinate. The composition may also if desired contain a pharmaceutically acceptable dye or colourant, and may, if desired, be coated using conventional film or sugar coating techniques.

If desired the composition may be formulated in sustained release form, e.g. by coating the active ingredient particles themselves or granules thereof made with for example sucrose and of a size up to 2 mm in diameter with a layer of, e.g. beeswax, Carnauba wax, stearic or palmitic acids, cetyl alcohol or similar substances which could be expected to be slowly dissolved or digested or to act as semi-permeable membranes through which the active ingredient can diffuse when the preparations are ingested. The composition may contain active ingredient particles or granules which are uncoated in admixture with particles or granules having one or more coats of the coating medium, and may be in the form of a capsule containing the particles or granules or alternatively a tablet, for which other adjuvants may be required, such as glidants or lubricants. The active ingredient may be administered as an enteric coated composition to make the active ingredient available at the appropriate part of the gastro-intestinal tract. This may be achieved by coating the tablet with a continuous film of material which is resistant and impermeable to gastric secretions, but which is susceptible to intestinal secretions. Typical film materials are shellac and its derivatives and cellulose acetate phthalate.

The active ingredient may, if desired, be used in specific form, e.g. having a substantial number of particles of effective particle size of less than 10 microns or particular crystal habit.

The active ingredient may also be formulated as an aqueous, e.g. a water: chloroform (400:1), solution containing from 0.001 to 10.0% by weight of the active ingredient. The free acid of formula I may conveniently be administered as an aqueous suspension containing from 0.1 to 10%, e.g. about 2%, by weight of the drug.

We prefer tablet formulations comprising active ingredient, in combination with a lubricant and a diluent, the lubricant and diluent containing no material capable of causing and adverse reaction in an allergic patient.

The tablet formulation preferably also contains a flow aid and/or a binder, the flow aid and/or the binder containing no material capable of causing an adverse reaction in an allergic patient.

The material capable of causing an adverse reaction in the patient may be a material, e.g. lactose, which can cause an adverse reaction through an enzyme deficiency in certain individuals or may be a material which contains residual traces of an anti-biotic such as penicillin or may be a material containing an actually or potentially allergenic material.

Material which is not actually or potentially allergenic is material which will not result in increased hypersensitivity of the individual treated to the material. The material should not be capable of eliciting an immune response, either anti-body or cell mediated. The material should also not combine with protein to form a hapten carrier system and should not activate the complement pathways in formation of C5a or C3a.

We particularly prefer there to be no proteinaceous material in the formulation. Examples of materials which are preferably excluded from the formulation are gelatin, starch, starch derivatives (e.g. sodium starch glycollate) and acacia. Materials which contain traces of protein because of their origin, e.g. lactose; or method of manufacture, e.g. maltose-dextrose combinations produced by enzyme treatment (and sold under the Trade Mark Emdex) are also preferably excluded from the formulation.

The formulation of the table may comprise the steps of wet granulation, dry granulation, melting moulding, enteric coating, film coating or formation into controlled release form. However we prefer to use a composition which can be compressed into a tablet directly without an intermediate, e.g. a wet or dry granulation, stage.

The flow aid may be, for example, purified talc or silicon dioxide and especially colloidal silicon dioxide having a mean particle size of about 12 mm.

The binder may be, for example, polyvinylpyrrolidone or methyl cellulose.

The lubricant may be, for example, stearic acid, a metallic stearate, a polyethylene glycol of molecular weight of 4,000 or more, or purified talc.

The diluent, which may also serve as disintegrant, may be microcrystalline cellulose, or a cellulose derivative, e.g. a cellulose ether such as methyl cellulose; or sodium bicarbonate or dibasic calcium phosphate. The formulation may also comprise a disintegrant as an entity separate from the diluent. When the disintegrant is a separate entity it should contain no material capable of causing an adverse, e.g. allergic reaction, in a patient.

The tablet formulation may be made by dry mixing the active ingredient with the other ingredients, e.g. the flow aid, binder, lubricant and diluent/disintegrant, for example in a powder blending machine. The mixing may be carried out in two stages, the blend, or parts thereof, being sieved through an appropriate screen (e.g. 60 mesh, 250 micron) at the end of a first stage in order to disperse any persistant aggregates. The sieved powder may then be mixed further. The resulting mixture may then be compressed in a tablet forming machine.

We prefer to use the free carboxylic acid of formula I as it is more orally acceptable than the derivatives thereof.

We prefer the tablet formulation to contain less than 50%, and preferably between about 0.5 and 18% by weight of active ingredient. Unexpectedly even with very small proportions of active ingredient we have found that a lubricant is highly desirable. We prefer the lubricant to comprise up to 4.0%, and preferably 0.2 to 4.0%, by weight of the composition. We also prefer the composition to contain between about 0.1 and 5.0%, e.g. about 0.5%, by weight of the flow aid. We prefer the binder to comprise from about 0.5 to 5% by weight of the composition, and the diluent/disintegrant to comprise from about 80 to 99% by weight of the composition.

We prefer tablet formulations containing from 3 to 15%, and more preferably from 4 to 10% by weight of water as such formulations have advantageous flow and compression characteristics.

The dosage to be administered will of course vary with the condition to be treated, with its severity and with its location. However in general a dosage of from about 1 to 50 mg, preferably 2 to 12 mg, and more preferably 3 to 6 mg, of the active ingredient (measured as free compound of formula I) administered 1 to 4 times a day (i.e. a daily dosage of 1 to 200 mg) is found to be satisfactory. The administration preferably takes place before meals.

Psychiatric conditions which may be treated by the method of our invention include those in which allergy or immune reactions (notably of the GI tract) play a contributory part, and in particular alcoholism, depression, mania, thought disorders, hallucinations, schizophrenia, manic depression and behavioural problems, e.g. hyperactivity in children or adolescents.

Other features which are of assistance in the diagnosis of patients with psychiatric symptoms who are suitable for treatment according to the invention include weight fluctuation, hyperhydrosis (sweating), palpitations and cravings for certain types of food. The symptoms demonstrated by suitable patients also tend to fluctuate within a few days or months, and standard therapies have often been of little help, although patients responding to standard therapies may also be treated by the method of the invention.

When treating behavioural problems, e.g. hyperactivity the patients are preferably children or adolescents, e.g. of up to the age of 18. The symptoms associated with such patients may be described as follows:

A. Necessary and Sufficient Symptoms

Hyperactivity - with a high and conspicuous level of gross motor activity (locomotion; or 'rump' hyperactivity when seated, i.e. squirming, changing position and getting up and down frequently; but not finger-hand twisting, picking or other small muscle activity) occurring across environments in situations in which sedentary or quiet behaviour is appropriate for age; and Disorder of attention - with higher distractability and shorter attention span than appropriate for chronological age (not mental age), especially in school or group situations.

B. Symptoms Commonly Associated, but not Sufficient for Diagnosis

1. Poorly integrated and labile behaviour, which gives the impression of immaturity and of uneven, but generally inadequate abilities.

2. Extremely variable relation to adults (including examiner), with rapid fluctuation from attempts at compliance to silly clowning, boisterous, mischievous or impertinent behaviour, clinging and demanding behaviour and/or angry or sullen negativism.

3. Labile affect. Reacts with excessive irritability to any situation interpreted as rejecting, demanding or restricting, with angry, suspicious, anxious, unhappy and silly clowning responses, often associated with gross motor discharge, tantrums, destructive or aggressive behaviour.

4. Speech is often sparse and unelaborated with a tendency to evade emotionally charged material.

5. Fantasy is usually expressed more clearly in play; concerned with movement and aggression, diffuse fears of retaliation and loss of love.

6. Motility usually variable, impulsive and poorly co-ordinated. Movements are relatively undifferentiated for age; has difficulty suppressing gross body movement when attempting isolated, finely co-ordinated finger-hand or arm movements. Body manipulation relatively uninhibited for age, chewing, sucking, nose picking, masturbation.

7. Unable to conform to demands of a group situation with peers; often becomes scapegoat and/or participates peripherally by provocative, wily, teasing, aggressive, quarrelsome behaviour; usually considered 'baby' and 'pest' by peers.

8. Adults usually consider him/her immature, demanding, difficult to manage. Has chronic and recurring difficulties in adapting to age-appropriate social and educational demands.

The above mentioned compound may of course be used in the form of its pharmaceutically acceptable, e.g. its sodium, potassium, calcium, magnesium or piperidine salts. It may also be used in the form of its ethyl ester, or of its simple amide derived from ammonia.

We claim

1. A method of treatment of psychiatric conditions in mammals which method comprises administration of an effective amount of a compound of the formula I,

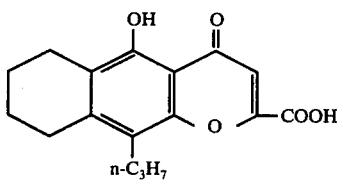

or a therapeutically acceptable salt, alkyl C 1 to 10 ester, mono-alkyl C 1 to 10 amide, di-alkyl C 1 to 10 amide or an unsubstituted amide thereof, as active ingredient, to a patient suffering from such a condition.

2. A method according to claim 1, wherein the active ingredient is the free acid of formula I.

3. A method according to claim 1, wherein the active ingredient is administered orally.

4. A method according to claim 1, wherein from 1 to 50 mg of active ingredient, measured as free compound of formula I, is administered from 1 to 4 times a day.

5. A method according to claim 4, wherein from 2 to 12 mg of active ingredient, measured as free compound of formula I, is administered from 1 to 4 times a day.

6. A method according to claim 5, wherein from 3 to 6 mg of active ingredient, measured as free compound of formula I, is administered from 1 to 4 times a day.

7. A method according to claim 1, wherein from 1 to 200 mg of active ingredient, measured as free compound of formula I, is administered per day.

8. A method according to claim 1, wherein the psychiatric condition to be treated is selected from alcoholism, depression, mania, thought disorders, hallucinations, schizophrenia, manic depression and behavioural problems.

9. A method according to claim 1, wherein the active ingredient is administered in the form of a tablet.

10. A method according to claim 1, wherein the active ingredient is administered before meals.

* * * * *